United States Patent [19]

Jassawalla et al.

[11] Patent Number: 4,581,018

[45] Date of Patent: Apr. 8, 1986

[54] IMPLANTABLE INFUSION DEVICE

[75] Inventors: Jal S. Jassawalla, San Francisco; Herbert Chen, Kensington, both of Calif.

[73] Assignee: Novacor Medical Corporation, Oakland, Calif.

[21] Appl. No.: 555,031

[22] Filed: Nov. 23, 1983

Related U.S. Application Data

[63] Continuation-in-part of Ser. No. 464,918, Feb. 8, 1983, abandoned, which is a continuation of Ser. No. 284,719, Jul. 20, 1981, abandoned.

[51] Int. Cl.⁴ .............................................. A61M 5/00
[52] U.S. Cl. .................................. 604/153; 604/155; 604/891
[58] Field of Search ............... 604/131, 134, 140, 141, 604/150, 153–155, 891

[56] References Cited

U.S. PATENT DOCUMENTS

| | | | |
|---|---|---|---|
| 3,731,681 | 5/1973 | Blacksher et al. | 604/141 |
| 3,884,228 | 5/1975 | Hahn | 604/141 |
| 3,951,147 | 3/1977 | Tucker et al. | 604/891 |
| 4,157,716 | 6/1979 | Rüegg | 128/DIG. 1 |
| 4,221,219 | 9/1980 | Tucker | 604/141 |
| 4,274,558 | 6/1981 | Clausen | 604/183 |
| 4,360,019 | 11/1982 | Portner et al. | 604/141 |

Primary Examiner—Stephen C. Pellegrino
Assistant Examiner—Mario Costantino
Attorney, Agent, or Firm—Fitch, Even, Tabin & Flannery

[57] ABSTRACT

An improved implantable infusion device for delivering precisely regulated doses of fluid into the body of a patient is disclosed. The device utilizes a resilient non-compliant pump bellows that is directly coupled by a gear train to a motor. The bellows is biased toward the expanded position and this factor, combined with the mechanical inertia of the gear train, substantially eliminates the danger of an overdose of infusate being released into the patient.

11 Claims, 2 Drawing Figures

IMPLANTABLE INFUSION DEVICE

This invention is a continuation-in-part of U.S. patent application Ser. No. 464,918, filed Feb. 8, 1983, now abandoned, which in turn is a continuation of U.S. patent application Ser. No. 284,719, filed July 20, 1981, now abandoned.

This invention relates to an improved implantable infusion device for delivering precisely regulated doses of fluid into the body of a patient. More specifically, the invention relates to an improved implantable infusion device which substantially eliminates the danger of an overdose of infusate being released into the patient.

Many types of implantable infusion devices are known and available. For example, U.S. Pat. No. 3,731,681, issued to Blackshear et al, discloses an implantable infusion pump utilizing recycling vapor-liquid constant pressure energy as its power source. A similar device is shown in U.S. Pat. No. 3,951,147 issued to Tucker et al. While such systems may be potentially useful for applications requiring continuous infusion at a uniform rate, they are not suitable for applications where the patient or his doctor must have some control over the timing and dosage of the infusate. The need for such control is increasing as more is learned about the numerous environmental, physiological, and psychological factors that influence a patient's need for, and response to, a given medication at a given time.

U.S. Pat. No. 4,152,098, issued to Moody et al, discloses a micropump that can be used in conjunction with reservoirs of pharmaceuticals implanted in a patient's body. Such a pump is inexpensive and simple to manufacture, and can be controlled by the patient. However, since the pump mechanism is separate and distinct from the reservoir containing the pharmaceutical to be infused, if a pump component fails, there is a possibility of patient overdoes from an accidental release of infusate from the reservoir.

In U.S. Pat. No. 4,221,219 to Tucker, there is shown a type of infusion pump which, as was the case in U.S. Pat. No. 3,051,147 mentioned above, employs a metal collapsible bellows which collapses on an infusate to expel the infusate through a catheter. Unlike the earlier patent, the device shown in U.S. Pat. No. 4,221,219 employs a solenoid actuated valve for controlling release of the infusate in precisely measured doses. In both the patents referred to in this paragraph, the motive power for expelling the contents of the reservoir confined within the collapsible bellows is provided by a reservoir of pressurized gas contained within the space between the collapsible bellows and a housing. This gas provides a constant force on the bellows tending to collapse the bellows and expel the contents thereof.

In these and other implantable infusion pumps wherein the motive expelling force is provided by a pressurized gas, the danger of accidental release of infusate into the patient is significant. In the event of a failure of the means which regulate the flow from the bellows into the catheter, continuous discharge of the contents of the bellows can occur. Similar catastrophic results can occur upon failure of the septum through which the bellows are refilled with infusate. Gas pressurized devices also suffer accuracy problems as a result of changes in ambient pressure, such as might occur when the patient takes an airplane trip.

Thus, there is a need for an improved implantable infusion device having the reservoir containing the infusate so constructed that if a component of the device fails, there is no danger of patient overdose. Also, to meet the needs of increasing numbers of patients who must control the timing and dosage of drugs being infused, there is a need for an improved implantable infusion device capable of delivering precise quantities of infusate, as and when needed by the patient.

Therefore it is an object of the present invention to provide an improved implantable infusion device which avoids accidental patient overdose resulting from the release of infusate if a component of the device should fail.

A further object of the present invention is to provide an improved implantable infusion device that can be controlled by the patient so that the fluid infusate can be dispensed as and when needed by the patient.

Another object of the present invention is to provide an improved implantable infusion device capable of delivering precise quantities of fluid.

Other objects and advantages of the present invention will become apparent to those skilled in the art from the following description taken in conjunction with the accompanying drawings wherein.

Figure 1:
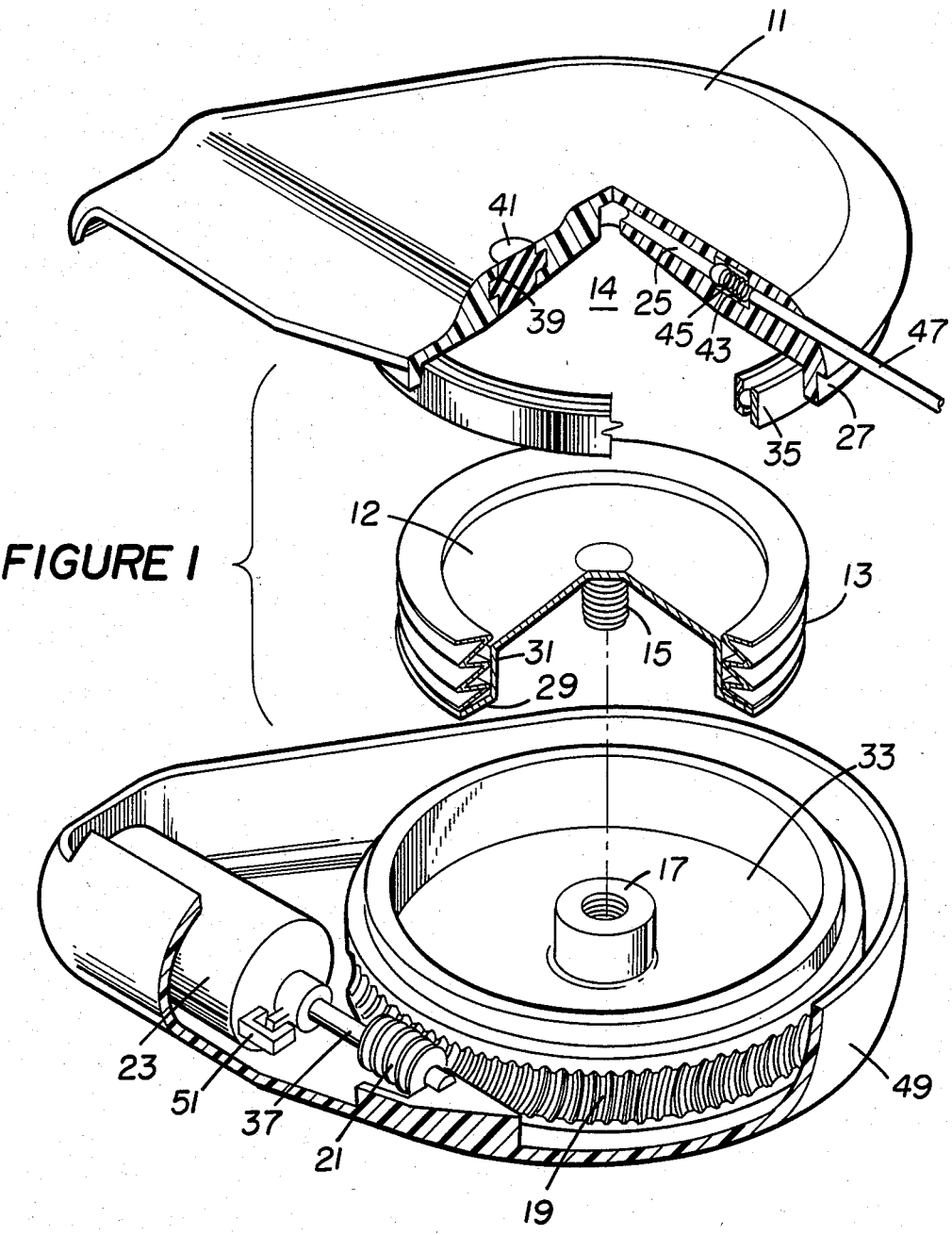
FIG. 1 is an exploded view, partially sectioned, of an improved implantable infusion device constructed in accordance with the invention.
Figure 2:
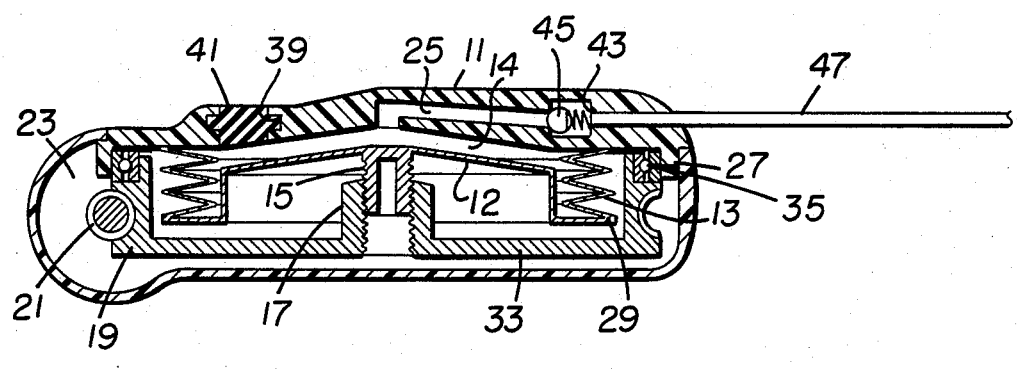
FIG. 2 is a full cross-sectional view of the improved implantable infusion device of FIG. 1.

Very generally, the improved implantable infusion device of the invention comprises means 11, 12 including a collapsible bellows 13 defining a reservoir 14. The bellows are directly coupled by a gear train 15, 17, 19 and 21 to a rotary motor 23. Upon incremental collapse of the bellows 13, caused by the rotary motion of the motor 23, a constant volume of fluid is infused through a passage 25 into the patient.

More specifically in the preferred embodiment of the present invention, the infusate is contained by a top cover or bulkhead 11 which comprises a generally circular plate of varying thickness. Near the periphery of the bulkhead, an annular lip 27 extends downwardly for reasons explained below. The thickest portion of the bulkhead 11 is provided with the internal passage 25, which is in fluid communication with the reservoir 14.

The reservoir 14 is also defined by a circular plate or bellows cap 12 from the periphery of which extends the collapsible bellows 13. The bellows are comprised of a suitable metal which is capable of repeated flexure at the folds of the bellows but which is sufficiently rigid so as to be noncompliant to variations in pressure within the reservoir. The bellows is also resilient with the bias being toward the expanded condition in which the reservoir volume is at its maximum. The lower end of the cylindrical bellows is secured to an annular flange 29 which extends outwardly from a periphery of a cylindrical wall 31, the opposite end of which is secured to the outer periphery of the circular bellows cap 12. The upper end of the bellows 13 is secured to the underside of the bulkhead 11 to define the reservoir 14.

A fine-pitched lead screw 15 is attached to the bellows cap 12 and extends downwardly from the center thereof. The lead screw 15 engages a threaded cylindrical drive bushing 17. The bushing 17 is secured to the center of a circular base plate 33. The outer periphery of the base plate 33 is secured to an annular worm wheel 19. The worm wheel 19 is supported for rotation around the common axis of the bellows 13 and the lead screw 15 and bushing 17, by an annular ball bearing 35. The bearing 35 is supported from the bulkhead 11 at the lip 27. Rotation of the worm wheel 19, is caused by the motor 23 through the worm 21 on the motor shaft 37. This advances the lead screw 15 and hence the bellows cap 12, compressing the bellows 13 to reduce the volume of the reservoir 14.

The bulkhead 11 is provided with an opening 39 therein in which a refill septum 41 is disposed. The refill septum is comprised of a fluid impermeable material which is capable of being repeatedly punctured by a hypodermic syringe for the purpose of refilling the reservoir 14 as will be explained below. In order to conduct the infusate from the reservoir 14 to the patient, the passage 25 in the bulkhead extends from a region central to the reservoir 14 at the bulkhead to the periphery of the bulkhead. An outlet valve chamber 43 containing an outlet valve 45 is also provided in the bulkhead. The outlet valve 45 is preferably biased closed at a pressure in the range of from slightly above zero to about four psi. A catheter 47 is joined in communication with the passage 25 in the bulkhead 11 in order to conduct fluid to an infusion site in the patient. The bellows 13, the gear train, and the motor 23, are all enclosed in a hermetically sealed rigid case 49 of a suitable biocompatible, biostable material such as metal or inert plastic. The case extends from and is sealed to the bulkhead, which is comprised of a similar material to thus form a biologically inert implantable system.

Upon incremental collapse of the bellows 13 as the result of the rotary motion of the motor 23, a constant volume of fluid is infused through the passage 25 and the catheter 47 into the patient. Because the collapsible bellows 13 are mechanically locked via the gear train 15, 17, 19 and 21 to the motor 23, infusate will not be released into the patient if a component of the device fails. Additional safety in the event of failure is provided due to the aforementioned resiliency of the bellows 13. Because the bellows are biased toward the position wherein the reservoir 12 is at maximum volume, the motor compresses the bellows against the bias. In the event of failure of the drive system, the bias of the bellows is toward expansion of the reservoir, thus insuring that the pressure in the reservoir will not increase and in fact will probably decrease, and preventing the expelling of infusate into the patient.

Additionally, the space between the bellows 13 and the outer casing 49 is maintained at or below atmospheric pressure when the infusate reservoir 14 is full. Thus, as the motor compresses the bellows, the pressure in this region decreases even further. This supplements the total force on the bellows tending to restore the bellows to maximum reservoir volume. The motor thus provides the motive force to overcome the resilient loading of the bellows itself, as well as to overcome the force exerted by the partial vacuum in the space between the bellows and the casing. In the event of a drive train failure, both the foregoing features provide a tendency for the bellows to expand the volume of the reservoir, thus preventing injection of infusate. The motor 23 is preferably a rotary motor. Such a motor can be powered by either an internal or external power source. For example, the motor can be powered and controlled by a system such as the one disclosed in co-pending U.S. patent application Ser. No. 135,219. If the power source is internal, it can be contained within the rigid case 49 with other parts of the device. It can also be enclosed within a separate biocompatible rigid case.

The collapsible bellows 13 is preferably comprised of a corrosion-resistant welded metal. Since the bellows 13 is noncompliant and mechanically locked via the gear train to the motor 23, accuracy of the device is insensitive to changes in temperature and pressure. The bellows cap 12 and the bulkhead of the housing are also comprised of a rigid corrosion-resistant material.

Assuming that infusate is present in the reservoir 14, conduction of infusate to the infusion site through the catheter 47 is accomplished by energization of the motor to reduce the volume of reservoir 14. As a result, infusate in the reservoir 14 is expelled past the outlet valve 45 and through the catheter 47 to the infusion site within the patient. The outlet valve 45 is preloaded to a low pressure to prevent diffusion and backflow into the reservoir 14.

In the preferred embodiment each revolution of the motor 23 advances the bellows a fixed distance, resulting in a constant stroke volume of infusate being delivered into the patient. An encoder 51 on a motor shaft along with its associated circuitry counts the number of revolutions of the rotary motor 23, thus providing an incremental indication of volume of infusate delivered from the reservoir 14.

In the operation of the preferred embodiment, a fixed amount of infusate is automatically delivered in accordance with energization of the motor 23. This may be accomplished automatically by a suitable implanted programmed controller, not shown, or may be accomplished by a suitable external controller, also not shown. The energy source may be an implanted battery powered pulse system, not shown, or may be derived transcutaneously from an external source, also not shown. For example, a system of the type disclosed in U.S. Pat. No. 4,360,019, issued Nov. 23, 1982 may be used. The cycle counter will count the number of times infusate is released from the reservoir 14 and indicates when the reservoir is empty. In the empty position, the bellows are collapsed, and the bellows cap 12 is in contact with the bulkhead 11. This expels any air which may have been in the reservoir. It also facilitates initial priming of the pump. In the preferred embodiment the bellows cap 12 is convex and the bulkhead 11 is concave, with the outlet to the passage 25 at the apex of the concavity. This allows bubbles to be readily purged from the reservoir 14 when the device is held upright during initial priming.

To refill the reservoir 14, a container of infusate, not shown, vented to atmospheric pressure and having a hypodermic needle attached, is connected to the reservoir 14 by piercing the refill septum 41. The refill septum 41 can be comprised of any suitable sealing material such as inert rubber or plastic. The motor 23 may then be energized to expand the bellows 13 until the reservoir 14 is filled. The full position may be determined by counting the number of revolutions of the motor 23 by the cycle counter. To insure that air does not enter the reservoir 14 during the filling process, a suitable filter, not shown, can be placed just upstream of the hypodermic needle.

Although the drive mechanism of the preferred embodiment comprises a rotary motor 23 and a worm 21 and worm wheel 19, a drive bushing 17 and a lead screw 15, other types of gear train arrangements may be used to transfer the energy from the rotary motor 23 to the bellows 13 within the contemplation of this invention. Any gear train system can be used between the motor and the bellows as long as sufficient force is supplied to the bellows to overcome the hydraulic load, the force required to compress the bellows and the force required to overcome the partial vacuum created in the space between the bellows and the outer casing. Because of the natural mechanical tendency of the gear train to resist displacement, failure of the system has a low probability of resulting in substantial motion of any of the internal parts. This also minimizes the likelihood of the expelling of the infusate upon failure.

The implantable infusion device of the instant invention is a low-pressure system, preferably operating at a less than 4 psi difference in the reservoir on ejection, thereby minimizing the possibility of leaks or catastrophic failure. Because the pump is a non-compliant metal bellows operating at low pressure, inaccuracy due to compressibility of air is minimized. In addition, air in the pump will be purged when the bellows reaches the empty position. Accuracy is also insensitive to changes in temperature and pressure (altitude), since the bellows are non-compliant and mechanically locked via the gear train.

The specific embodiments described herein are given by way of example only and the invention includes the many modifications and variations that will be apparent to those skilled in the art from the foregoing disclosure.

What is claimed is:

1. An improved implantable infusion device for delivering a precisely regulated amount of infusate into the body of a patient, comprising, means defining a reservoir for containing the infusate to be infused, said reservoir defining means including a collapsible bellows comprised of non-compliant material and being movable between a full position and a collapsed position, said bellows being resiliently biased toward said full position, means defining a passage for conducting said infusate from said reservoir to an infusion site within the body of the patient in direct response to incremental collapse of said bellows, drive means for incrementally collapsing said bellows in accordance with a preselected infusate dosage rate, said drive means comprising a motor, and a gear train which mechanically locks said bellows to said motor, and housing means at least partially enclosing said bellows and forming with said bellows a hermetically sealed volume arranged to accommodate expansion of said bellows, said sealed volume being at or below atmospheric pressure for all positions of said bellows from said full position to said collapsed position, said housing means comprising a rigid outer case comprised of biocompatible and biostable material, said case enclosing and substantially hermetically sealing the moving parts of said reservoir defining means and said drive means.

2. An implantable infusion device according to claim 1 wherein said reservoir defining means further comprise a refill septum pierceable with a hypodermic needle.

3. An implantable infusion device according to claim 1 wherein said passage defining means include an outlet valve.

4. An implantable infusion device according to claim 3 wherein said outlet valve is preloaded to a pressure of up to 4 psi.

5. An implantable infusion device according to claim 1 wherein said passage defining means include a catheter.

6. An implantable infusion device according to claim 1 wherein said collapsible bellows are further comprised of a corrosion resistant welded metal.

7. An improved implantable infusion device for delivering a precisely regulated amount of infusate into the body of a patient, comprising, means defining a reservoir for containing the infusate to be infused, said reservoir defining means including a collapsible bellows comprised of non-compliant material and being movable between a full position and a collapsed position, means defining a passage for conducting said infusate from said reservoir to an infusion site within the body of the patient in direct response to incremental collapse of said bellows, drive means for incrementally collapsing said bellows in accordance with a preselected infusate dosage rate, said drive means comprising a motor, and a gear train which mechanically locks said bellows to said motor, said gear train comprising a worm gear and a worm wheel, said worm gear being directly driven by said rotary motor, and housing means at least partially enclosing said bellows and forming with said bellows a hermetically sealed volume arranged to accommodate expansion of said bellows, said sealed volume being at or below atmospheric pressure for all positions of said bellows from said full position to said collapsed position, said housing means comprising a rigid outer case comprised of biocompatible and biostable material, said case enclosing and substantially hermetically sealing the moving parts of said reservoir defining means and said drive means.

8. An implantable infusion device according to claim 7 comprising a lead screw attached to said bellows, a threaded drive bushing engaged with said lead screw, and means connecting said drive bushing to said worm wheel so that said lead screw advances as said worm wheel is rotated by said motor to displace said bellows.

9. An implantable infusion device according to claim 8 including ball bearing means supporting said worm wheel for rotation on said housing.

10. An implantable drug infusion device according to claim 1 including a cycle counter for counting the rotations of said rotary motor.

11. An implantable drug infusion device according to claim 1 wherein said reservoir defining means are so shaped as to permit reduction of the volume of the reservoir substantially to zero to thereby expel the contents thereof including air bubbles through said passage.

* * * * *